US00PP14311P39

(12) United States Plant Patent
Goemans

(10) Patent No.: US PP14,311 P3
(45) Date of Patent: Nov. 18, 2003

(54) ALSTROEMERIA PLANT NAMED 'SOPHIE'

(50) Latin Name: *Alstroemeria hybrid*
Varietal Denomination: Sophie

(75) Inventor: Robert Adrian Goemans, Chichester (GB)

(73) Assignee: Wulfinghoff Alstroemeria B.V., Rijswijk (NL)

( * ) Notice: Subject to any disclaimer, the term of this patent is extended or adjusted under 35 U.S.C. 154(b) by 0 days.

(21) Appl. No.: 10/097,254

(22) Filed: Mar. 15, 2002

(65) Prior Publication Data

US 2003/0177559 P1 Sep. 18, 2003

(51) Int. Cl.[7] ..... A01H 5/00

(52) U.S. Cl. ..... Plt./309

(58) Field of Search ..... Plt./309

*Primary Examiner*—Kent Bell
*Assistant Examiner*—Louanne Krawczewicz Myers
(74) *Attorney, Agent, or Firm*—Foley & Lardner

(57) ABSTRACT

A new and distinct Alstroemeria plant named 'Sophie' characterized as suitable for pot size larger than 7 cm; growth height 10–30 cm under greenhouse conditions; bushy-dwarf growth habit; pale purple flowers with a yellow base, black stripes on at least 1 to 2 tepals; and 3 weeks inflorescence longevity on the plant, 2 weeks as a cut flower.

1 Drawing Sheet

Latin name of the genus and species of the plant claimed: Alstroemeria hybrid.
Variety denomination: 'Sophie'.

BACKGROUND OF THE NEW VARIETY

The present invention comprises a new and distinct cultivar of Alstroemeria plant, hereinafter referred to by the cultivar name 'Sophie'.

'Sophie' originated from a hybridization made in a controlled breeding program in Chichester in Sussex, United Kingdom by the inventor Robert Adrian Goemans. The female parent is an unnamed, unpatented, cultivar from a cross between *Alstroemeria aurea* 'Lutea' and *Alstroemeria pelegrina* 'Alba'. The male parent of 'Sophie' is an unnamed selection of a dwarf Butterfly type cultivar (unpatented).

'Sophie' was discovered and selected as one flowering plant within the progeny of the stated parentage by Robert Adrian Goemans in 1998 in a controlled environment in Chichester, United Kingdom. The first act of asexual reproduction of 'Sophie' was accomplished when vegetative cuttings were taken from the initial selection in May, 1999 in a controlled environment in Chichester, United Kingdom. Horticultural examination of selected plants initiated in 1999 has demonstrated that the combination of characteristics as herein disclosed for 'Sophie' are firmly fixed and retained through successive generations of asexual reproduction.

BRIEF SUMMARY OF THE INVENTION

The following traits have been repeatedly observed and are determined to be basic characteristics of which in combination distinguish this Alstroemeria as a new and distinct cultivar:

1. Suitable for pots larger than 7 cm;
2. Growth height 10–30 cm under greenhouse conditions;
3. Bushy-dwarf growth habit;
4. Pale purple flowers with a yellow base, black stripes on at least 1 to 2 tepals; and 5. 3 weeks inflorescence longevity on the plant, 2 weeks as a cut flower.

There are no commercial cultivars known to the inventor, similar in comparison to 'Sophie'. In comparison to 'Sophie', the female parental cultivar is tall and has a pale yellow color; and the male parental cultivar is very small in size and blue in color.

'Sophie' has not been observed under all possible environmental conditions. The phenotype may vary significantly with variations in environment such as temperature, light intensity and day length, without any change in genotype. The following observations, measurements and comparisons describe plants grown in Chichester, Sussex, United Kingdom under greenhouse conditions which approximate those generally used in commercial practice.

BRIEF DESCRIPTION OF THE DRAWINGS

The accompanying photographic drawing shows a typical plant of the new variety with colors as accurate as is possible with drawings of this type.

The photographic drawing shows the flowers and foliage of 'Sophie'.

DETAILED BOTANICAL DESCRIPTION

In the following description, color references are made to The Royal Horticultural Society Colour Chart (R.H.S.). The color values were determined in the afternoon of Sep. 28, 2001 under normal daylight conditions in Wateringen, The Netherlands. The plants described are nine months of age and grown in 15 cm pots.

Classification:
*Botanical.*—Alstroemeria hybrid.
*Commercial.*—Alstroemeria cv. Sophie.
Plant:
*Form.*—Pot Plant.
*Height.*—10–30 cm (Dutch greenhouse conditions).
*Diameter.*—22 cm.

*Growth.*—Bushy-dwarf growth habit.

*Time it takes to produce a flowering plant.*—From planting of rooted tissue cultured rhizomes to flowering is 6 to 9 months, depending on cultural conditions.

*Lateral branches.*—28 per plant, 9 cm in length, 4 mm diameter; internode length 7 mm, color RHS green-yellow 144 D.

Foliage:

*Quantity.*—5–10 leaves on each centimeter of stem, depending on growth stage.

*Size of leaf.*—Length: 35–50 mm; width: 15 mm.

*Shape of leaf.*—Oblong-ovate; cuspidate apex; cuneate base; dentate margin.

*Texture.*—Silky.

*Color.*—Upper side is dark green, RHS 137 A. Underside is light-green, RHS 137 C.

Rhizomes:

*Color.*—White RHS 158 A to RHS 158 D.

*Size.*—Length 10–50 mm; diameter 6–15 mm, depending on age.

Inflorescence:

*Number of flowers per cyme.*—2–3.

*Number of flowers per umbel.*—2–3.

*Number of flowers per plant.*—12–15.

*Number of flowers per lateral stem.*—3.

*Flowering season.*—May–September under outdoor conditions.

*Fragrance.*—None.

Bud:

*Form.*—Tubular pointed.

*Diameter.*—10–20 mm.

*Length.*—15–25 mm.

*Peduncle.*—20 mm, medium-green RHS 144 A to RHS 144 B.

*Color.*—Red, RHS 65 A to RHS 65 B with green RHS 145 B to RHS 145 D.

Flower:

*Size.*—Medium, length: 40–60 mm; width: 40–60 mm.

*Shape.*—Broad obovate.

Tepals:

*Quantity.*—3.

*Size.*—Length: 68 mm, width: 30 mm.

*Apex.*—Emarginate.

*Base.*—Cuneate.

*Margin.*—Serrate.

*Texture.*—Silky.

*Upper surface color.*—Purple, RHS 65 A to RHS 65 D; Yellow from middle to base, RHS 11A to RHS 11D (on at least 1 to 2 tepals).

*Under surface.*—Yellow at the base, RHS 11 A to RHS 11 D.

*Other notations.*—Black stripes RHS 202 A.

Peduncle:

*Length.*—40 mm.

*Color.*—Medium-green, RHS 144 A to RHS 144 B.

Lasting quality: 3 weeks on the plant; 2 weeks as a cut flower.

Reproductive organs:

*Stamens.*—6 .

*Anthers.*—Yellow, RHS 13 A.

*Pollen.*—Plentiful, greyed-yellow RHS 162 C.

*Filaments.*—Red, RHS 65 A to RHS 65 D.

*Pistils.*—1, color red-pink, RHS 65 A to RHS 65 D.

*Stigma.*—Pink-white, RHS 36 A to RHS 36 C.

*Seeds.*—None.

Disease/pest resistance/susceptibility: No known information.

I claim:

1. A new and distinct cultivar of Alstroemeria plant named 'Sophie', as described and illustrated herein.

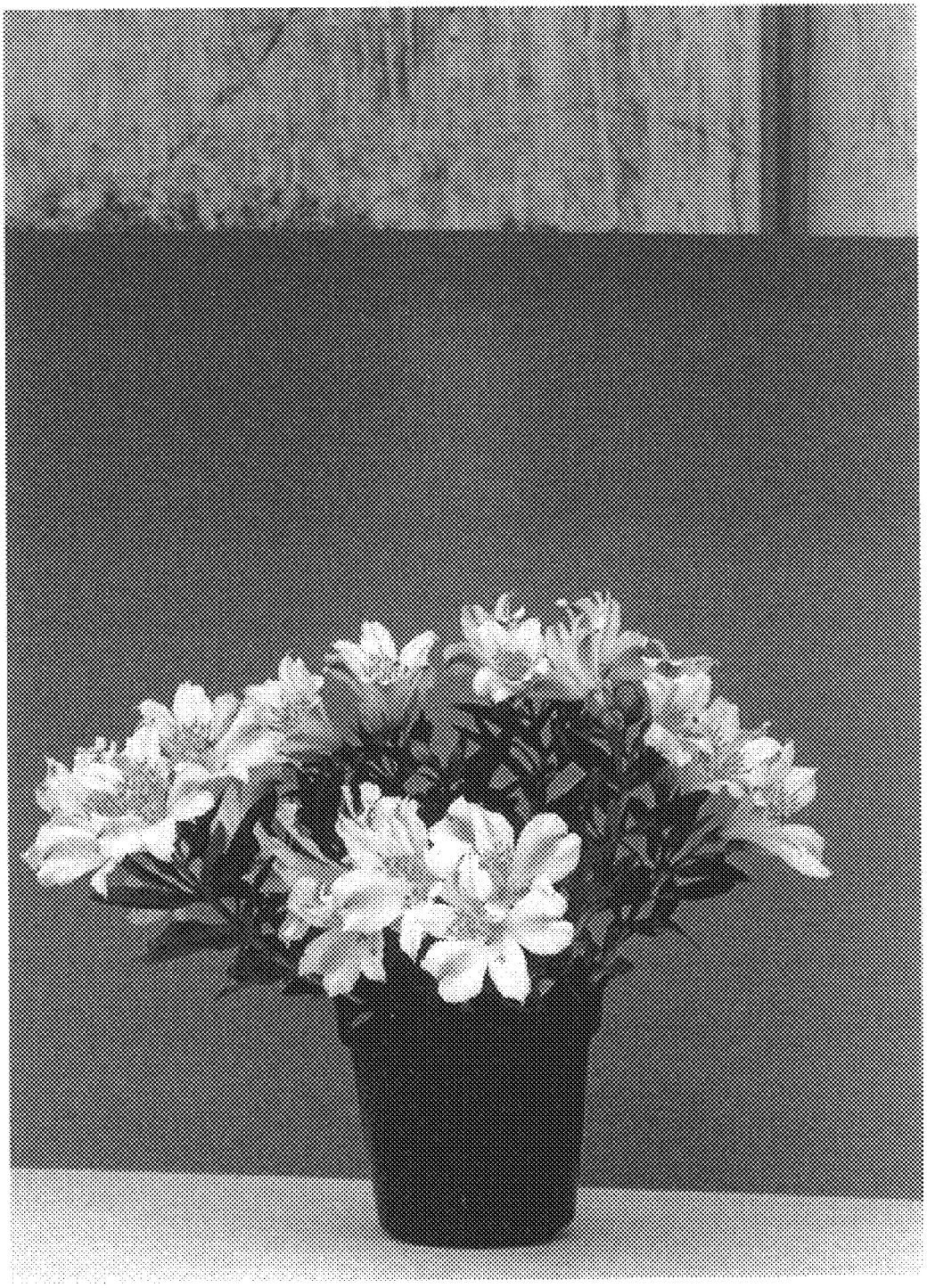

* * * * *